United States Patent [19]

Abou-Gharbia et al.

[11] Patent Number: 4,716,166
[45] Date of Patent: Dec. 29, 1987

[54] HISTAMINE H1 ANTAGONISTS

[75] Inventors: Magid A. Abou-Gharbia; Susan T. Nielsen, both of Wilmington, Del.; Michael B. Webb, King of Prussia, Pa.

[73] Assignee: American Home Products Corporation, New York, N.Y.

[21] Appl. No.: 921,553

[22] Filed: Oct. 21, 1986

[51] Int. Cl.$^4$ ............... C07D 473/08; A61K 31/52
[52] U.S. Cl. .................... 514/265; 544/269; 544/272; 544/267
[58] Field of Search ........... 544/276, 272, 277, 269; 514/265

[56] References Cited

U.S. PATENT DOCUMENTS

| | | | |
|---|---|---|---|
| 4,426,383 | 1/1984 | Sugimoto et al. | 424/253 |
| 4,564,617 | 1/1986 | Sugimoto et al. | 544/269 |
| 4,603,204 | 7/1986 | Thiele et al. | 544/269 |

Primary Examiner—Nicholas S. Rizzo
Attorney, Agent, or Firm—Richard K. Jackson

[57] ABSTRACT

Histamine H$_1$-receptor antagonists of the formula:

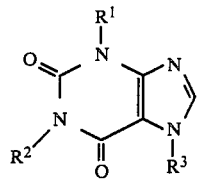

where R$^1$ is hydrogen or alkyl; one of R$_2$ and R$^3$ is alkyl and the other is

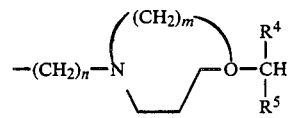

where R$^4$ is pyridin-2-yl, pyridin-4-yl, thienyl, or phenyl, any of which is optionally substituted by a halo, alkyl of 1 to 6 carbon atoms, nitro, trifluoromethyl, hydroxy or alkoxy of 1 to 6 carbon atoms substituent; and R$^5$ is pyridin-2-yl, pyridin-4-yl or phenyl, any of which is optionally substituted by a halo, alkyl of 1 to 6 carbon atoms, alkoxy of 1 to 6 carbon atoms, nitro or trifluoromethyl substituent.

8 Claims, No Drawings

HISTAMINE H1 ANTAGONISTS

BACKGROUND OF THE INVENTION

U.S. Pat. No. 4,426,383 discloses a group of theophylline derivatives which serve as vasodilators useful for increasing blood flow in the treatment of circulatory insufficiency. The compounds are also disclosed to control blood platelet aggregation, act on the central nervous system (psychic energizers), provide antihistamine, analgesic, anti-asthmatic and hypotensive actions.

DESCRIPTION OF THE INVENTION

In accordance with this invention there is provided a group of histamine $H_1$-antagonists of the formula:

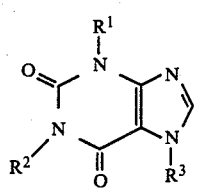

in which
$R^1$ is hydrogen or alkyl of 1 to 6 carbon atoms;
one of $R^2$ and $R^3$ is alkyl of 1 to 6 carbon atoms and the other is

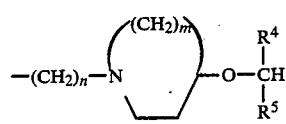

where
$R^4$ is pyridin-2-yl, pyridin-4-yl, thienyl, or phenyl, any of which is optionally substituted by a halo, alkyl of 1 to 6 carbon atoms, nitro, trifluoromethyl, hydroxy or alkoxy of 1 to 6 carbon atoms substituent;
$R^5$ is pyridin-2-yl, pyridin-4-yl or phenyl, any of which is optionally substituted by a halo, alkyl of 1 to 6 carbon atoms, hydroxy, alkoxy of 1 to 6 carbon atoms, nitro or trifluoromethyl substituent;
n is one of the integers from 2 to 10;
and m is one of the integers 1, 2 or 3.
or a pharmaceutically acceptable salt thereof.

The preferred compounds are those in which $R^1$ is alkyl of 1 to 6 carbon atoms, $R^4$ and $R^5$ are phenyl, hydroxyphenyl or halophenyl (fluorine and chlorine being the most preferred halogens), n is one of the integers 2, 3, 4 or 5 and m is 2.

The pharmaceutically acceptable salts of the histamine $H_1$ antagonists of this invention are prepared by conventional means with inorganic or organic acids such as hydrochloric, hydrobromic, sulfuric, phosphoric, nitric, acetic, fumaric, citric, tartaric, maleic, lactic, 2-hydroxyethanesulfonic, methanesulfonic, toluene-4-sulfonic, ethanesulfonic acid, and the like.

The compounds of this invention may be prepared by a variety of synthetic routes using conventional methods. Thus, theophylline derivatives in which $R^1$ and $R^2$ are methyl can be prepared by reacting theophylline with a suitable dihalo lower alkane to yield an intermediate product. This intermediate can be reacted with 4-hydroxypiperidine in dimethylformamide in the presence of sodium bicarbonate to afford the unsubstituted piperidinyltheophylline intermediate which then can be reacted with the appropriately substituted bis(phenyl) methyl halide in dimethylformamide in the presence of triethylamine to afford the desired product, thusly:

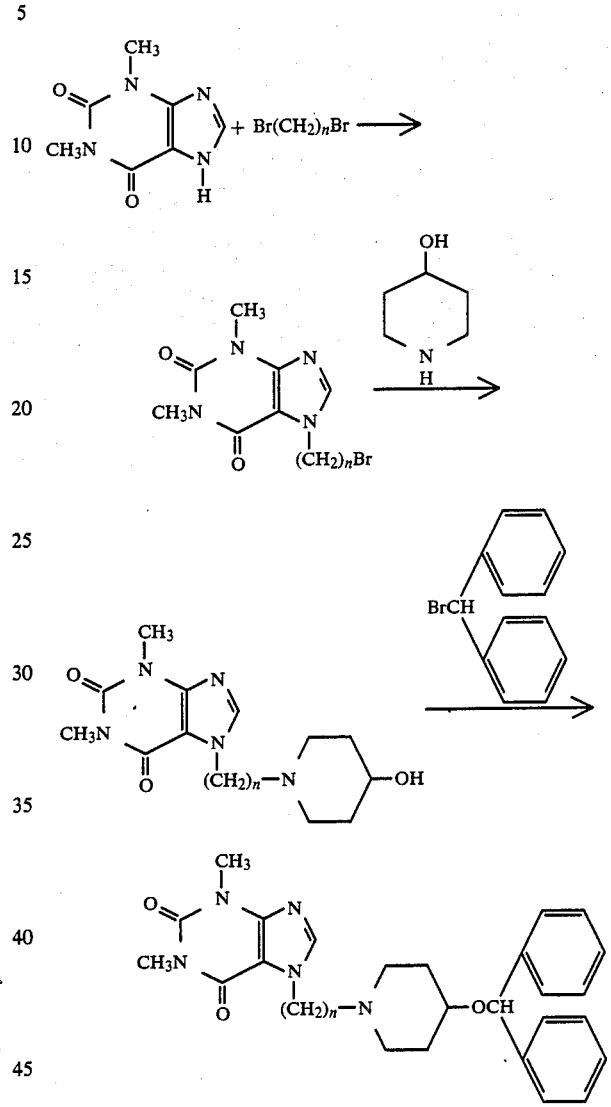

The following examples illustrate the preparation of representative compounds of the invention.

EXAMPLE 1

7-[3-(4-Diphenylmethoxy)-1-piperidinyl]propyl-3-7-dihydro-1-3,dimethyl-1H-purine-2,6-dione A solution of theophylline (10.0 g, 0.0555 mol), 1,3-dibromopropane (11.6 ml, 23.1 g, 0.114 mol) and triethylamine (10.5 ml, 7.62 g, 0.0753 mol) in N,N-dimethylformamide (250 ml) was stirred at 60° C. overnight. The stirring was continued one day at room temperature. The solvent was evaporated under reduced pressure. The residue was suspended in $CH_2Cl_2$ and water. An emulsion was caused by a fine solid suspended in the mixture. The solid was filtered out and discarded. The aqueous layer was extracted three times with $CHCl_3$. The combined organic layers were dried with $MgSO_4$. Evaporation of the solvent under reduced pressure gave 7-(3-bromopropyl)-3,7-dihydro-1,3-dimethyl-1H-purine-2,6-dione (12.8 g, 77% yield).

7-(3-Bromopropyl)-3,7-dihydro-1,3-dimethyl-1H-purine-2,6-dione (4.0 g, 0.013 mol), 4-hydroxypiperidine (1.3 g, 0.013 mol), and NaHCO$_3$ (2.0 g, 0.024 mol) were stirred in dimethylformamide (50 ml) at 140° C. overnight. The mixture was then refluxed for an additional day. The dimethylformamide was evaporated under reduced pressure. The residue was insoluble in water and CH$_2$Cl$_2$ and was dissolved in aqueous HCl. The solution was filtered and the separated solid was discarded. The filtrate was basified with aqueous NaOH and the solution was extracted with CH$_2$Cl$_2$. The extracts were combined and dried with MgSO$_4$. The solvent was evaporated and the residue was purified by HPLC to give 7-[3-(4-hydroxy)-1-piperidinyl]propyl-3,7-dihydro-1,3-dimethyl-1H-purine-2,6-dione (1.3 g, 31% yield).

7-[3-(4-Hydroxy-1-piperidinyl)]propyl-3,7-dihydro-1,3-dimethyl-1H-purine-2,6-dione (1.15 g, 3.58 mmol) and diphenylmethylbromide (1.80 g, 7.28 mmol) were added to a suspension of NaHCO$_3$ (0.80 g, 9.5 mmol) in dimethylformamide (60 ml) and the reaction mixture was refluxed overnight. The dimethylformamide was evaporated under reduced pressure and the residue was dissolved in CH$_2$Cl$_2$ and H$_2$O. The aqueous layer was extracted with CH$_2$Cl$_2$ and the combined CH$_2$Cl$_2$ extracts were dried with anhydrous MgSO$_4$. The solvent was evaporated under reduced pressure and the residue was purified by HPLC to give the desired product 7-[3-(4-diphenylmethoxy)-1-piperidinyl]-propyl-3,7-dihydro-1,3-dimethyl-1H-purine-2,6-dione (0.50 g, 29% yield).

The fumarate salt was prepared by dissolving the free base in EtOH and adding a solution of fumaric acid in EtOH. The crystalline product was filtered after standing at room temperature for 2 hours to afford the title compound; mp 183°–185° C.

Analysis for: C$_{28}$H$_{33}$N$_5$O$_3$·C$_4$H$_4$O$_4$·H$_2$O: Calculated: C, 61.82; H, 6.32; N, 11.27; Found: C, 61.6; H, 6.22; N, 11.27.

EXAMPLE 2

7-[3-[4-Bis(4-fluorophenyl)methoxy]-1-piperidinyl]propyl-3,7-dihydro-1,3-dimethyl-1H-purine-2,6-dione The title compound was prepared following the procedure of Example 1 with the exception that bis(4-fluorophenyl)methylbromide was used instead of diphenylmethylbromide. The free base was converted to the monofumarate salt; mp 195°–196° C.

Analysis for: C$_{28}$H$_{31}$F$_2$N$_5$O$_3$·C$_4$H$_4$O$_4$: Calculated: C, 60.08; H, 5.52; N, 10.95; Found: C, 59.95; H, 5.67; N, 11.81.

EXAMPLE 3

7-[2-(4-Diphenylmethoxy)-1-piperidinyl]ethyl-3,7-dihydro-1,3-dimethyl-1H-purine-2,6-dione The title compound was prepared following the procedure of Example 1 with the exception that 7-(2-bromoethyl)-3,7-dihydro-1,3-dimethyl-1H-purine-2,6-dione was used instead of 7-(3-bromopropyl)-3,7-dihydro-1,3-dimethyl-1H-purine-2,6-dione. The free base was converted to the monofumarate salt; mp 176°–181° C.

Analysis for: C$_{27}$H$_{31}$N$_5$O$_3$·C$_4$H$_4$O$_4$: Calculated: C, 63.09; H, 5.98; N, 11.88; Found: C, 62.50; H, 5.85; N, 12.20.

EXAMPLE 4

7-[2-[4-Bis(4-fluorophenyl)methoxy]-1-piperidinyl]ethyl-3,7-dihydro-1,3-dimethyl-1H-purine-2,6-dione The title compound was prepared following the procedure of Example 3 with the exception that bis(4-fluorophenyl)methylbromide was used instead of diphenylmethylbromide. The free base was converted to the monofumarate salt; mp 191°–195° C.

Analysis for: C$_{27}$H$_{29}$F$_2$N$_5$O$_3$·C$_4$H$_4$O$_4$: Calculated: C, 59.51; H, 5.32; N, 11.20; Found: C, 59.46; H, 5.49; N, 11.20.

The compounds of this invention were established to be histamine H$_1$- antagonists by subjecting them to the following standard test procedures for H$_1$- blocking activity:

Fresh segments of terminal ileum immediately proximal to Peyer's patch, obtained from male Buckshire guinea pigs, were suspended in 37° C. Tyrode's solution in a tissue bath and aerated. The tissue segments were placed under one gram tension and allowed to equilibrate for one hour. Histamine was added to each tissue bath to a final concentration of $1 \times 10^{-6}$M. The contraction response after it equilibrated was noted as grams tension. Test drug was added, in the presence of histamine, to each bath to a final concentration of $1 \times 10^{-7}$M. The change in grams tension was noted and the percent reduction in grams tension calculated.

Following this procedure, with quadruplicate sets of tissues, the compound of Example 1 demonstrated 92 percent reduction in tissue contraction and the compounds of Examples 2, 3 and 4 provided 70, 86 and 62 percent reduction in contraction, respectively.

In comparison when a complete histamine dose-response curve was carried out, the ileum tissues then exposed to the compound of Example 1 at a concentration of $10^{-8}$M and subsequently treated with histamine to repeat the original dose-response curve, a marked, parallel shift of the curve to the right was observed, thus evidencing the requirement for greatly increased histamine concentrations to induce the same tissue contraction. From this study, the histamine H$_1$ antagonist potency of the product of Example 1 was calculated via the formula $$K_B = \frac{[\text{Antagonist}]}{[\text{Dose Ratio} - 1]}$$

to equal $2.9 \times 10^{-10}$M.

In vivo, the compound of Example 1 blocked histamine-induced death in guinea pigs at the doses and after the oral pretreatment times (number of hours prior to histamine administration) shown in the Table.

TABLE

| Compound of Example 1 Dose, mg/kg, p.o. | Percent Survival | | | | | | |
|---|---|---|---|---|---|---|---|
| | 1 Hour | | | 2 Hours | 18 Hours | | |
| | Trial 1 | Trial 2 | Trial 3 | Trial 3 | Trial 4 | Trial 5 | Trial 6 |
| 0.5 | | | | | | 70 | 40 |
| 1.0 | 40 | 10 | 40 | 70 | 70 | 80 | |
| 5.0 | 80 | | | | | | |
| 10.0 | | | | 60 | | | |

From this data it can be seen that the representative compound of this invention produced in Example 1 was orally effective in reducing histamine-induced lethality in guinea pigs, the standard experimental animal, at 1, 2 and 18 hours after dosing, with greater efficacy at 18 hours indicating rapid onset of action, with a long duration of action.

The pharmacological results obtained characterize the compounds of this invention as $H_1$-receptor antagonists useful in the treatment of mammals experiencing conditions such as asthma, hay fever, allergic rhinitis, atopic dermatitis, conjunctivitis, pruritis, and eczema, or other responses where histamine is released and acts on $H_1$ receptors. As such, they may be administered topically or systemically. Topical administration is advantageously achieved to the skin via creams, ointments or lotions, or via aerosol introduction into the respiratory tract. Systemic administration may be orally, nasally, intrabronchially, parenterally or rectally. In each instance, conventional formulations amenable to use in the desired administration route is appropriate. Hence, tablets and capsules may be prepared for oral administration, suppositories for rectal administration, isotonic aqueous solutions for intravenous, subcutaneous or intramuscular injection and in aerosol suspensions for inhalation.

As is conventional in the use of antihistamine agents, the appropriate dosage is determined on a subjective basis by initial administration of small amounts, ca. 0.5–15 mg. followed by increasing quantities up to about 400 mg., depending upon the desired route of administration, until the desired symptomatic relief is obtained. The dosage is personalized in this manner for each patient, based upon size, age, type of discomfort, degree of disability, etc., by the physician.

What is claimed is:

1. A compound of the formula:

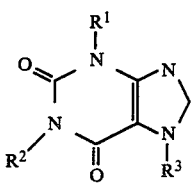

in which
R$^1$ is hydrogen or alkyl of 1 to 6 carbon atoms;
one of R$^2$ and R$^3$ is alkyl of 1 to 6 carbon atoms and the other is

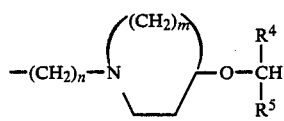

where
R$^4$ is pyridin-2-yl, pyridin-4-yl, thienyl, or phenyl, any of which is optionally substituted by a halo, alkyl of 1 to 6 carbon atoms, nitro, trifluoromethyl, hydroxy or alkoxy of 1 to 6 carbon atoms substituent;
R$^5$ is pyridin-2-yl, pyridin-4-yl or phenyl, any of which is optionally substituted by a halo, alkyl of 1 to 6 carbon atoms, hydroxy, alkoxy of 1 to 6 carbon atoms, nitro or trifluoromethyl substituent;
n is one of the integers from 2 to 10;
and m is one of the integers 1, 2 or 3,
or a pharmaceutically acceptable salt thereof.

2. A compound of claim 1 of the formula:

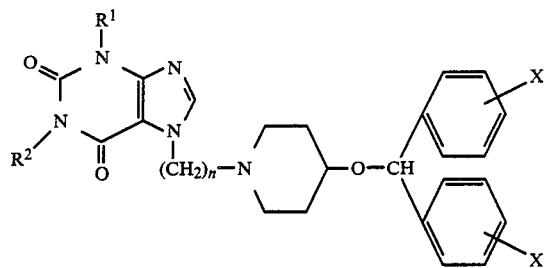

where
R$^1$ and R$^2$ are alkyl of 1 to 6 carbon atoms,
n is one of the integers 2, 3, 4, or 5, and each
x is hydrogen, hydroxy or a halogen,
or a pharmaceutically acceptable salt thereof.

3. The compound of claim 1 which is 7-[3-(4-Diphenylmethoxy)-1-piperidinyl]propyl-3-7-dihydro-1-3,dimethyl-1H-purine-2,6-dione, or a pharmaceutically acceptable salt thereof.

4. The compound of claim 1 which is 7-[3-[4-Bis(4-fluorophenyl)methoxy]-1-piperidinyl]propyl-3,7-dihydro-1,3-dimethyl-1H-purine-2,6-dione, or a pharmaceutically acceptable salt thereof.

5. The compound of claim 1 which is 7-[2-(4-Diphenylmethoxy)-1-piperidinyl]ethyl-3,7-dihydro-1,3-dimethyl-1H-purine-2,6-dione, or a pharmaceutically acceptable salt thereof.

6. The compound of claim 1 which is 7-[2-[4-Bis(4-fluorophenyl)methoxy]-1-piperidinyl]ethyl-3,7-dihydro-1,3-dimethyl-1H-purine-2,6-dione, or a pharmaceutically acceptable salt thereof.

7. A pharmaceutical composition comprising a histamine $H_1$-receptor antagonist amount of a compound of the formula:

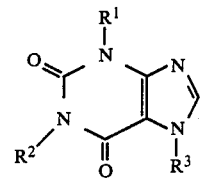

in which
R$^1$ is hydrogen or alkyl of 1 to 6 carbon atoms;
one of R$^2$ and R$^3$ is alkyl of 1 to 6 carbon atoms and the other is

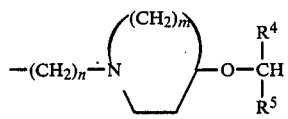

where
R$^4$ is pyridin-2-yl, pyridin-4-yl, thienyl, or phenyl, any of which is optionally substituted by a halo, alkyl of 1 to 6 carbon atoms, nitro, trifluoromethyl, hydroxy or alkoxy of 1 to 6 carbon atoms substituent;
R$^5$ is pyridin-2-yl, pyridin-4-yl or phenyl, any of which is optionally substituted by a halo, alkyl of 1 to 6 carbon atoms, hydroxy, alkoxy of 1 to 6 carbon atoms, nitro or trifluoromethyl substituent;
n is one of the integers from 2 to 10;

and m is one of the integers 1, 2 or 3,
or a pharmaceutically acceptable salt thereof, and a pharmaceutically acceptable carrier.

8. A method for preventing the symptoms resulting from histamine interaction with $H_1$ receptor sites which comprises administering to a mammal in need a histamine $H_1$-receptor antagonist amount of a compound of the formula:

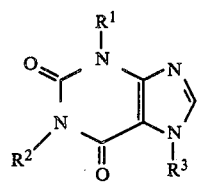

in which
$R^1$ is hydrogen or alkyl of 1 to 6 carbon atoms;
one of $R^2$ and $R^3$ is alkyl of 1 to 6 carbon atoms and the other is

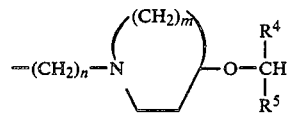

where
$R^4$ is pyridin-2-yl, pyridin-4-yl, thienyl, or phenyl, any of which is optionally substituted by a halo, alkyl of 1 to 6 carbon atoms, nitro, trifluoromethyl, hydroxy or alkoxy of 1 to 6 carbon atoms substituent;
$R^5$ is pyridin-2-yl, pyridin-4-yl or phenyl, any of which is optionally substituted by a halo, alkyl of 1 to 6 carbon atoms, hydroxy, alkoxy of 1 to 6 carbon atoms, nitro or trifluoromethyl substituent;
n is one of the integers from 2 to 10;
and m is one of the integers 1, 2 or 3,
or a pharmaceutically acceptable salt thereof.

* * * * *